United States Patent [19]

Kaiser et al.

[11] Patent Number: 4,927,346
[45] Date of Patent: May 22, 1990

[54] APPARATUS FOR DEPOSITING PARTICULATE MATERIAL INTO A PAD OF FIBROUS MATERIAL IN A FORMING CHAMBER

[75] Inventors: Thomas A. Kaiser, Vermilion; Douglas C. Mulder, Wellington, both of Ohio; David E. O'Ryan, Jackson, Mich.; Douglas A. Schneider, Lorain; Rodney L. Ward, Wellington, both of Ohio

[73] Assignee: Nordson Corporation, Westlake, Ohio

[21] Appl. No.: 348,149
[22] Filed: May 2, 1989

Related U.S. Application Data

[63] Continuation of Ser. No. 939,093, Dec. 8, 1986, abandoned.

[51] Int. Cl.5 .............................................. A29D 7/00
[52] U.S. Cl. .................................. 425/81.1; 118/308; 264/113; 425/83.1
[58] Field of Search ...................... 118/308, 62.2, 62.4; 239/704, 705, 706, 707, 124; 264/103, 113, DIG. 75; 406/3, 19, 61, 153; 425/73, 75, 80.1, 81.1, 83.1; 427/180, 421

[56] References Cited

U.S. PATENT DOCUMENTS

| | | | |
|---|---|---|---|
| 2,336,745 | 12/1943 | Manning | 264/DIG. 75 |
| 2,357,392 | 9/1944 | Francis, Jr. | 264/DIG. 75 |
| 3,669,103 | 6/1972 | Harper et al. | 128/156 |
| 3,670,731 | 6/1972 | Harmon | 128/284 |
| 3,792,943 | 2/1974 | Helgesson | 425/83.1 |
| 3,967,623 | 7/1976 | Butterworth et al. | 128/287 |
| 3,984,272 | 10/1976 | Teed | 156/201 |
| 4,005,957 | 2/1977 | Savich | 425/80.1 |
| 4,045,833 | 9/1977 | Mesek et al. | 128/287 |
| 4,118,531 | 10/1978 | Hauser | 428/224 |
| 4,123,211 | 10/1978 | Rudloff | 425/83.1 |
| 4,186,165 | 1/1980 | Aberson et al. | 264/112 |
| 4,319,870 | 3/1982 | Slama | 425/83.1 |
| 4,333,463 | 6/1982 | Holtman | 128/287 |
| 4,351,660 | 9/1982 | Plantard et al. | 65/5 |
| 4,364,992 | 12/1982 | Ito et al. | 428/283 |
| 4,381,783 | 5/1983 | Elias | 604/368 |
| 4,415,388 | 11/1983 | Korpman | 156/78 |
| 4,429,001 | 1/1984 | Kolpin et al. | 428/283 |
| 4,469,734 | 9/1984 | Minto et al. | 428/134 |
| 4,480,947 | 11/1984 | Nagasaka | 406/14 |
| 4,543,274 | 9/1985 | Mulder | 118/308 |
| 4,551,191 | 11/1985 | Kock et al. | 156/276 |
| 4,559,050 | 12/1985 | Iskra | 604/368 |
| 4,600,603 | 7/1986 | Mulder | 118/308 |
| 4,610,678 | 9/1986 | Weisman et al. | 604/368 |
| 4,640,810 | 2/1987 | Laursen et al. | 264/518 |
| 4,666,647 | 5/1987 | Enloe et al. | 264/121 |
| 4,675,209 | 6/1987 | Pedigrew | 427/194 |
| 4,724,114 | 2/1988 | McFarland et al. | 264/113 |

FOREIGN PATENT DOCUMENTS

| | | |
|---|---|---|
| 0007149 | 1/1980 | European Pat. Off. . |
| 0053928 | 6/1982 | European Pat. Off. . |
| 0085729 | 11/1985 | European Pat. Off. . |
| 0174775 | 3/1986 | European Pat. Off. . |
| 0198683 | 10/1986 | European Pat. Off. . |
| 1510427 | 10/1970 | Fed. Rep. of Germany . |
| 8209936.7 | 3/1982 | Fed. Rep. of Germany . |
| 2150033 | 6/1985 | United Kingdom . |

Primary Examiner—Jay H. Woo
Assistant Examiner—C. Scott Bushey
Attorney, Agent, or Firm—Wood, Herron & Evans

[57] ABSTRACT

An apparatus for forming a non-woven pad consisting of fibrous material in which highly moisture-absorbent particles are intermixed with the fibrous material throughout a predetermined portion of the thickness of the non-woven pad. The non-woven pad is formed atop a conveyor moving through a chamber which has a duct connected to a source of vacuum operable to draw fibrous material injected into the chamber onto the conveyor. A spray gun or an extension thereof is positioned within the chamber relative to the fibrous material atop the conveyor, and is operated to discharge moisture-absorbent material at a predetermined velocity, such that the moisture-absorbent material is intermixed with the fibrous material throughout preferably a center layer of the thickness of the non-woven pad while forming boundary layers on either side of the center layer which are substantially free of moisture-absorbent material. The spray gun preferably operated intermittently to form spaced, sharply defined areas along the length and width of the non-woven pad wherein each area has moisture-absorbent material interspersed throughout a portion of the thickness thereof.

26 Claims, 4 Drawing Sheets

APPARATUS FOR DEPOSITING PARTICULATE MATERIAL INTO A PAD OF FIBROUS MATERIAL IN A FORMING CHAMBER

This application is a continuation of application Ser. No. 939,093, filed Dec. 8, 1986, now abandoned.

BACKGROUND OF THE INVENTION

This invention relates to a method and apparatus for making moisture-absorbent substrates, and more particularly, to a method and apparatus for interspersing highly moisture-absorbent particles throughout a predetermined portion of a fibrous material pad in a non-woven product.

Hygenic articles such as disposable diapers, sanitary napkins, incontinence pads and sick bed sheets must have a high absorption capacity to effectively retain eliminated body fluids for acceptable periods of time. Early hygenic articles of this type employed cellulose wadding, fluff cellulose or absorbent cotton as absorbent materials. The problem with these materials is that their moisture-retaining capacity is relatively small compared to their volume. In order to improve the moisture-retaining capacity of hygenic articles made from these materials, the volume of such absorbent materials in the hygenic article must be increased. This produces a bulky product which is unacceptable in many hygenic articles, particularly sanitary napkins.

In an effort to reduce the volume and size of hygenic articles, and increase their absorbent capacity, fluid-absorbent substrates have been developed in which highly absorbent materials are combined within the fiber structure of cellulose fluff, wood pulp, textile fibers or other non-woven, fibrous materials. Many substantially water-insoluble absorbent polymers having a high capacity for absorbing water and body fluids have been developed in recent years for enhancing the moisture-absorbent capability of hygenic articles. These polymers are partially or wholly synthetic and are commercially available in fine grain, particulate form. See, for example, U.S. Pat. Nos. 3,997,484; 3,661,815; 4,117,222; and 3,936,441.

One system for incorporating a moisture-absorbent core or laminate in a diaper is disclosed, for example, in U.S. Pat. No. 3,984,272. The system of this patent includes a forming chamber having an inlet and outlet which is connected by a feed conduit to a source of fibrous material such as finely ground wood pulp. A perforated conveyor is movable through the forming chamber between its inlet and outlet above a duct located at the base of the forming chamber. The duct is connected to a source of vacuum which is operable to create a negative pressure within the forming chamber.

The fibrous material or fibers are injected into the forming chamber through the feed conduit and drawn onto the perforated conveyor by operation of the vacuum source. The fibers form a non-woven pad atop the conveyor whose density is controlled by the vacuum pressure and feed rate of the conveyor. The pad is then transmitted to a leveling or scarfing roller near the outlet of the forming chamber which is operable to remove at least a portion of the fibrous material at the top of the non-woven pad to produce a non-woven pad of uniform thickness. The non-woven pad is then transmitted by the conveyor through the outlet of the forming chamber for subsequent operations to form the completed hygenic article.

In addition to incorporating a moisture-absorbing pad or laminate in a diaper to produce a diaper having improved moisture-returning capabilities, there are also prior art methods for combining highly moisture-absorbent material with a non-woven pad. In one method, the moisture-absorbent material is injected into a feed conduit which directs the fibrous material into a forming chamber in an apparatus of the type disclosed in U.S. Pat. No. 3,984,272, as discussed above. The moisture-absorbent material and fibrous material are intermixed within the feed conduit to completely intersperse the moisture-absorbent material throughout the fibers prior to introduction into the forming chamber. This produces a non-woven pad atop the conveyor within the chamber in which the moisture-absorbent material is present throughout the entire thickness, width and length of the non-woven pad.

One problem with the above-described method is the loss of moisture-absorbent material through the perforated conveyor in the forming chamber. As the fibers and moisture-absorbent material mixture is drawn onto the perforated conveyor to form the non-woven pad, moisture-absorbent material at the lower portion of the non-woven pad is drawn through the conveyor into a filtering-reclamation system. A loss of about 20% of the moisture-absorbent material is not uncommon. Additionally, the moisture-absorbent material is difficult to contain, even within the filtering system, and environmental contamination can result.

A second problem with this method involves damage to the apparatus used in subsequent operations to form the finished hygenic article, particularly cutting devices. For example, in manufacturing disposable diapers, the non-woven pad must be cut to length and formed with leg holes by the operation of die cutters or other cutting devices. It has been found that the presence of moisture-absorbent material throughout the entire pad structure rapidly dulls die cutters which reduces their effective life substantially.

A third problem with this method is that the moisture-absorbent material is distributed throughout the non-woven pad across its entire length and width. This produces substantial waste because in subsequent forming operations the non-woven pad is cut to the desired length of the hygenic article. In addition, the application of moisture-absorbent material across the entire width of the non-woven pad may be unnecessary for some types of hygenic articles, particularly disposable diapers where the leg holes are cut at the edges of the layer.

Another prior art method of combining moisture-absorbent material with the non-woven pad described above comprises applying moisture-absorbent material to the top surface of the non-woven pad downstream from the leveling or scarfing roller and outside of the forming chamber. This has the advantage of eliminating waste of the moisture-absorbent material since there is no loss through the perforated conveyor. Wear on die cutters is still a problem, but not as serious a problem as the other method described above since only the top surface of the product contains the moisture-absorbent material.

One disadvantage of this method is that the moisture-absorbent capacity of the non-woven pad is substantially limited because the moisture-absorbent material is concentrated on the top of the pad. This causes so-called "gel blockage" wherein the moisture-absorbent material at the top of the non-woven pad becomes saturated with fluid and prevents the wicking or transfer of moisture to the remaining portion of the pad. As a result, the fluid is retained at the surface of the pad in contact with the wearer of the hygenic article causing discomfort. Hygenic articles made in accordance with the first method described above also exhibit this problem, to a lesser extent, because at least some of the moisture-absorbent material is located at the top of the non-woven pad.

A second disadvantage of this second method, and for that matter the first method described above, is migration of the moisture-absorbent material, particularly if it is combined with the non-woven pad in particulate form. The moisture-absorbent material in both methods of application is located, at least to some extent, near or at the top of the non-woven pad. In particulate or granular form, the moisture-absorbent material can be dislodged from the type of pads which are not sealed at the ends.

A third disadvantage of this second method is that application of the moisture-absorbent material atop the non-woven pad is performed outside of the forming chamber. This requires some type of collection system to capture the oversprayed material and prevent it from escaping to the environment. This adds expense to the system, and, if not properly designed, can lead to environmental contamination from the uncollected moisture-absorbent material.

SUMMARY OF THE INVENTION

It is therefore among the objectives of this invention to provide a method and apparatus for the formation of a pad of non-woven, fibrous material containing a second material such as moisture-absorbent material interspersed throughout a predetermined portion of the thickness of the non-woven pad which minimizes waste of the moisture-absorbent material, which maximizes the moisture-retaining capacity of the non-woven pad while limiting damage to die cutters and other apparatus employed in forming the finished hygenic article and which reduces contamination of the environment with oversprayed moisture-absorbent material.

These objectives are accomplished in a method of forming a non-woven pad of material in which the fibrous material such as fibers are introduced through a feed conduit into a forming chamber. A perforated conveyor is movable between the inlet and outlet of the forming chamber above a duct which is connected to a source of vacuum. The fibers are drawn onto the perforated conveyor by operation of the vacuum source. In the course of drawing the fibrous material atop the conveyor, one or more spray guns intermix highly moisture-absorbent material in powder, particulate or strand-like form with the fibrous material to form a non-woven pad having moisture-absorbent material interspersed throughout a predetermined portion of the thickness of the non-woven pad.

In the presently preferred embodiment, the duct within the forming chamber applies a vacuum therein such that the thickness of the fibrous material atop the conveyor progressively increases from a minimum depth at a point where the vacuum is first applied to the perforated conveyor, to a maximum depth located near one or more scarfing rollers which function to level the pad to a finished thickness. In one aspect of this invention, moisture-absorbent material is intermixed with the fibrous material as the fibrous material is drawn onto the perforated conveyor to form a non-woven pad in which the distribution of moisture-absorbent material is concentrated within a predetermined portion of the thickness of the pad.

Desired distribution of the moisture-absorbent material is achieved by a two-stage adjustment procedure involving the positioning and operation of the spray gun. Initially, the spray gun or an extension thereof is positioned within the forming chamber above the fibrous material atop the conveyor. The location of the spray gun along the length of the conveyor is chosen to intermix the moisture-absorbent material with the fibrous material at a predetermined thickness of the fibrous material atop the conveyor. As mentioned above, the thickness of the fibrous material atop the conveyor progressively increases from the point at which vacuum is first applied to the perforated conveyor, to a point near the scarfing roller. If a concentration of moisture-absorbent material is desired near the bottom of the non-woven pad, the spray gun is preferably positioned near the point at which vacuum is first applied, i.e., where the fibrous material is relatively thin. This allows the moisture-absorbent material to intermix with the fibrous material forming the lower portion of the non-woven pad, and thereafter additional fibers fill in atop the lower portion to form the finished pad. A concentration of moisture-absorbent material nearer the top of the non-woven pad is obtained by initially positioning the spray gun closer to the scarfing roller where the fibrous material is thicker and the pad more completely formed. In that case, the moisture-absorbent material intermixes with the fibers near the top of the pad and only a relatively small amount of fibers thereafter fill in to form the completed pad.

The positioning of the spray gun relative to the fibrous material atop the conveyor is an initial or gross adjustment in obtaining the desired distribution of moisture-absorbent material within the nonwoven pad. A more precise or finer adjustment of the moisture-absorbent material distribution within the non-woven pad is made by varying the velocity at which the moisture-absorbent material is ejected from the spray gun. Depending upon the location of the spray gun, and the distribution desired, the velocity of the moisture-absorbent material is controlled to cause the material to penetrate to a greater or lesser extent within the fibrous material to form a non-woven pad having a concentration of moisture-absorbent material throughout a predetermined thickness or layer thereof.

In one presently preferred embodiment, the spray gun or an extension thereof is positioned relative to the fibrous material atop the conveyor, and the velocity of the moisture-absorbent material discharged from the spray gun is controlled, so that an article is produced in which the moisture-absorbent material is interspersed in the center portion or layer of the non-woven pad of fibrous material. Preferably, the moisture-absorbent material is spaced from both the top and bottom surfaces of the non-woven pad a distance approximately equal to at least about 10% of the thickness of the finished pad. This prevents moisture-absorbent material from being removed from the top of the pad by the scarfing roller and redistributed in other areas of the non-woven product or lost through the perforated conveyor, while ensuring that the diaper has good overall moisture-retaining capability. By allowing at least 10% of pad formation on the bottom before introducing the moisture-absorbent material, the fibrous pad itself prevents loss of moisture-absorbent material through the perforated conveyor. Those portions of the non-woven pad at the top and bottom are therefore substantially free of moisture-absorbent material.

Dispersion of the moisture-absorbent material within a center layer of the non-woven pad in the manner described has several advantages. First, damage to die cutters and other equipment employed in subsequent manufacturing operations is reduced because the moisture-absorbent material can be distributed throughout only a portion of the length and thickness of the non-woven pad. Secondly, by spacing the moisture-absorbent material from the top of the non-woven pad, it is not removed as the scarfing rollers level the top portion of fibrous material to form a pad of finished thickness. This prevents loss of moisture-absorbent material through the perforated conveyor in the forming chamber while ensuring that the non-woven pad has good overall moisture-retaining capability. Additionally, so-called "gel blockage" is substantially reduced because the moisture-absorbent material is not located at the top surface of the pad but begins beneath the surface at a thickness of at least about 10% of the overall pad thickness. This allows moisture to flow or wick away from the surface of the pad in contact with the wearer for added comfort. Finally, since spraying of the moisture-absorbent material is conducted within the forming chamber, escape of such material is substantially prevented and environmental contamination is thus minimized.

In another aspect of this invention, the spray gun is operable to control the width of the pattern of moisture-absorbent material injected into the non-woven pad of fibrous material. Additionally, the spray gun is operable intermittently to form spaced areas along the non-woven pad with no moisture-absorbent material where the layer is cut in the formation of the individual hygenic articles. Both the controlled pattern width and intermittent operation of the spray gun reduces waste of moisture-absorbent material, and saves wear on die cutters and other cutting devices, without detracting from the moisture-retaining capability of the hygenic article being formed.

In one presently preferred embodiment, the spray gun comprises a gun barrel having a discharge end and an inlet end connected to a source of air-entrained moisture-absorbent material, preferably in particulate form. A first air flow amplifier is positioned along the gun barrel downstream from its inlet end which is connected to a high velocity stream of compressed air. The first air flow amplifier is operable to direct a high velocity stream of air generally upstream of the gun barrel, toward the inlet. This evenly distributes the moisture-absorbent material throughout the airstream as it moves through the gun. In addition, upstream movement of air from the first air flow amplifier prevents drifting of the moisture-absorbent material toward the discharge end of the gun when the flow of moisture-absorbent material is terminated such as during intermittent operation of the gun or when the gun is turned off at the end of a cycle.

A second air flow amplifier is positioned in the gun barrel downstream from the first air flow amplifier which is also connected to a high velocity stream of compressed air. The second air flow amplifier is operable to impact the air-entrained moisture-absorbent material flowing through the gun barrel with the high velocity stream of compressed air to accelerate the moisture-absorbent material for ejection from the discharge end of the gun barrel to the fibrous material forming the non-woven pad.

Preferably, the spray gun of this embodiment is operated intermittently by alternately terminating the flow of moisture-absorbent material to the inlet of the gun, and then restarting the flow, while continuing the supply of high velocity compressed air to the first air flow amplifier. This provides spaced areas along the non-woven pad in which the moisture-absorbent material is interspersed with the fibers, and areas on the non-woven pad having no moisture-absorbent material.

In an alternative embodiment of a spray gun employed in the method of this invention, intermittent distribution of moisture-absorbent material within the fibrous material forming the non-woven pad is also provided. The spray gun of this embodiment comprises a manifold formed with an internal cavity, a vent passageway connecting the internal cavity to atmosphere, and an inlet passageway, an outlet passageway and a return passageway all connected to the internal cavity. The inlet passageway communicates with the feed hopper containing moisture-absorbent material in powder or particulate form in which a rotating auger or screw feeder is mounted. The rotating screw feeder is operable to transport a metered quantity of the moisture-absorbent particles through the inlet passageway into the internal cavity of the manifold.

A first air flow amplifier is formed with an inlet connected to the outlet passageway of the manifold, and an outlet connected to a discharge conduit which extends into the forming chamber above the non-woven pad. A delivery line from a source of high velocity compressed air is connected to an annular channel formed in the first air flow amplifier. The first air flow amplifier is operable to create a vacuum within the internal cavity of the manifold which draws ambient air through the vent passageway and into contact with the moisture-absorbent material from the feed hopper to form a stream of air-entrained moisture-absorbent material within the internal cavity. The first air flow amplifier sucks the air-entrained stream of moisture-absorbent material out of manifold, and impacts the stream with high velocity compressed air. In the course of passage through the first air flow amplifier, the air-entrained moisture-absorbent material is accelerated and then ejected through the discharge conduit for intermixing with the fibrous material forming the non-woven pad.

In the preferred embodiment, a second air flow amplifier is mounted to the return passageway of the manifold which cooperates with the first air flow amplifier to provide for intermittent discharge of moisture-absorbent material for intermixing with the fibrous material forming the non-woven pad. The second air flow amplifier functions to draw moisture-absorbent material introduced into the internal cavity of the manifold for recirculation back to the feed hopper. In order to eject moisture-absorbent material, flow of compressed air to the second air flow amplifier is closed while flow of compressed air to the first air flow amplifier is opened. This permits discharge of the moisture-absorbent material through the first air flow amplifier to the fibrous material forming the non-woven pad. Discharge of moisture-absorbent material is terminated by closing the flow of high velocity compressed air to the first air flow amplifier while simultaneously opening the flow of high velocity compressed air to the second air flow amplifier.

Both of the spray guns described above are formed with a discharge end through which air-entrained moisture-absorbent material is ejected for intermixing with the fibrous material forming the non-woven pad. In one method of practicing this invention, the spray guns are positioned exteriorly of the forming chamber and an elongated conduit is connected to their discharge ends which extends into the forming chamber immediately above the fibrous material atop the perforated conveyor. Depending upon the width of the pattern of moisture-absorbent material desired, the discharge end of the conduit may include a nozzle having a deflector or a restrictor. Where relatively wide patterns are desired, a nozzle having an internal deflector is preferably mounted to the discharge end of the conduit. Narrow patterns are obtained with a nozzle having a restrictor associated therewith.

In one preferred embodiment, the nozzle comprises an annular sleeve formed with a throughbore within which an internal deflector is concentrically mounted. The internal deflector is formed with a radially outwardly extending, generally conical-shaped end portion. The outer end of the annular sleeve of the nozzle also has a conical shape which is generally parallel to the end portion of the deflector. Moisture-absorbent material flowing through the annular sleeve is deflected radially outwardly by the end of the internal deflector. The extent of such radial movement is limited, however, by contact of the material with the parallel, conical-shaped outer wall of the annular sleeve to control the width of the pattern discharging into the non-woven pad of fibrous particles.

In some instances, it is desirable to position a spray gun of this invention within the forming chamber, e.g., to accommodate space considerations or the like. In the event a nozzle is employed on the discharge end of the gun barrel of the first spray gun described above, for example, it is preferable to encase such spray gun with a closed housing having a vent communicating with the exterior of the forming chamber. The air flow amplifiers mounted to the gun barrel of this spray gun draws ambient air into the gun barrel in the course of impacting the moisture-absorbent material with a stream of high velocity compressed air. If no enclosure or housing is provided for the spray gun, fiber-laden air within the forming chamber is drawn through the gun and clogs the nozzle. In one embodiment, a cannister is fitted about the spray gun and the cannister-spray gun unit is mounted within the forming chamber. In an alternative embodiment, a duct extends into the chamber within which the spray gun is mounted to isolate the spray gun from the fiber-laden air in the chamber.

In another aspect of this invention, air-entrained, moisture-absorbent material is supplied to either of the spray guns disclosed herein by a self-contained cartridge feeder. In one preferred embodiment, the cartridge feeder comprises a housing having a closed interior formed with a pressure relief door, a fluidized bed mounted at the base of the housing and an inlet for receiving moisture-absorbent material. The fluidized bed is connected by a pump to the inlet of the gun barrel in the first spray gun described above to provide an air-entrained stream of moisture-absorbent material for discharge therethrough.

In an alternative embodiment of the cartridge feeder, the fluidized bed and pump are eliminated. The housing is open at the bottom and mounted directly atop a feed hopper of the type described above which carries a rotatable auger or screw feeder. In this form, the cartridge feeder is employed with the spray gun having the mainfold as described above.

Both of the embodiments of the cartridge feeder described above require venting of the interior of the housing to prevent a pressure buildup therein. For this purpose, a clean air chamber is mounted to the housing of each of the embodiments of the cartridge feeder described above. The clean air chamber is formed with an inlet which communicates with the interior of the housing, and an outlet located exteriorly of the housing. A cartridge filter is mounted to the inlet of the clean air chamber which extends into the interior of the housing. The outlet of the clean air chamber is connected to a source of vacuum, such as the vacuum source at the base of the forming chamber herein.

In operation, a vacuum is applied to the clean air chamber which draws air from the interior of the housing to provide a vent. Any moisture-absorbent material which is free floating within the housing of the cartridge feeder, is filtered by the cartridge filter so that it remains in the housing and is not expelled to atmosphere.

DESCRIPTION OF THE DRAWINGS

The structure, operation and advantages of the preferred embodiment of this invention will become further apparent upon consideration of the following description, taken in conjunction with the accompanying drawings, wherein.

DETAILED DESCRIPTION OF THE INVENTION

Figure 1A:
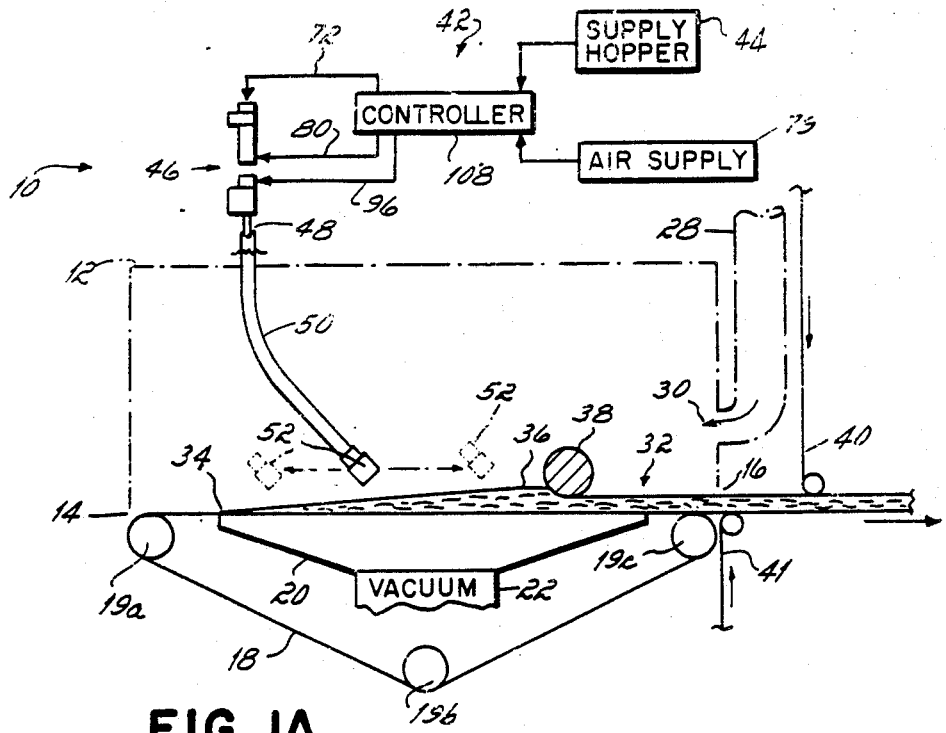
FIG. 1a is a schematic, elevational view of one embodiment of the method and apparatus of this invention.
Figure 2:
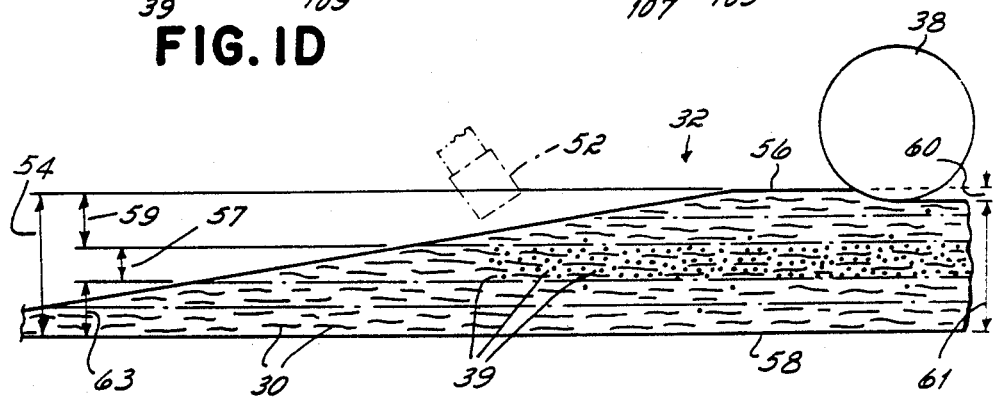
FIG. 2 is an enlarged, partial view of the non-woven pad being formed within the forming chamber herein.

Referring now to FIGS. 1a and 2, an apparatus 10 for forming a pad of non-woven, fibrous material having moisture-absorbent material interspersed throughout a portion of the pad is illustrated. The apparatus 10 comprises a forming chamber 12 having an inlet 14 and an outlet 16. An endless perforated conveyor 18 carried by three rollers 19a–c is movable through the forming chamber 12 between its inlet 14 and outlet 16 in the direction indicated by the arrows in FIG. 1a. The conveyor 18 is movable over a duct 20 mounted at the base of forming chamber 12 which is connected to a vacuum source 22.

A fiber supply conduit 28 is connected to the conveyor outlet end of forming chamber 12 at a position above the conveyor 18. The fiber supply conduit 28 is connected to a source (not shown) of fibrous material preferably in the form of particles or fibers 30, shown by arrows in FIG. 1a, such as cellulose fluff, wood pulp, textile fibers or other fibrous particulate materials. See also FIG. 2. The fibers 30 are pulled into the forming chamber 12 and drawn onto the conveyor 18 by operation of the vacuum source 22. As illustrated in FIG. 1a, vacuum is applied within duct 20 which causes fibers 30 to be drawn onto the conveyor 18 between the inlet end of forming chamber 12, where the duct 20 begins, and the outlet end of the forming chamber 12 where the duct 20 ends. As the conveyor 18 moves through the forming chamber 12, the thickness of the intertwined fibers 30 drawn onto the conveyor 18 gradually increases from a point 34 of minimum thickness near the inlet 14 of forming chamber 12 where the vacuum is initially applied, to a point 36 of maximum thickness downstream from point 34.

As shown in FIGS. 1a and 2, and discussed in more detail below, a levelling or scarfing roller 38 is rotatably mounted within the forming chamber 12 near the outlet 16. The scarfing roller 38 is operable to remove an upper portion of the fibers 30 to form a non-woven pad 32 of fibers 30 having the desired finished thickness for discharge through the outlet 16 of the forming chamber 12. Upon exiting the forming chamber 12, the non-woven pad 32 is combined with a top sheet 40 and a bottom sheet 41 to form an hygenic article (not shown).

A principle feature of this invention is the intermixing of highly moisture-absorbent material with a selected portion of the fibers 30 to form a non-woven pad 32 in which the moisture-absorbent material is interspersed throughout a predetermined portion of the thickness of the non-woven pad 32. The moisture-absorbent material employed herein is illustrated in the FIGS. as granules or particles 39; it is contemplated, however, that the moisture-absorbent material could take other forms such as strands or the like. See FIG. 2.

Referring again to FIGS. 1a and 2, one presently preferred embodiment of a spray gun system 42 for intermixing moisture-absorbent material with a selected portion of the fibers 30 forming the non-woven pad 32 is illustrated schematically for purposes of describing the method herein. The spray gun system 42 includes a spray gun 46 having an inlet communicating with a supply hopper 44 and an outlet 48 connected to an elongated tube 50 such as formable hydraulic tubing. The tube 50 extends into the forming chamber 12 and has a nozzle 52 mounted at its discharge end. The spray gun 46 is operable to discharge moisture-absorbent material in particulate form from its outlet end 48, through the tube 50 and into the forming chamber 12. In turn, the moisture-absorbent particles 39 are ejected from the nozzle 52 at the discharge end of the tube 50 and intermixed with the fibers 30 on the conveyor 18. The spray gun system 42 per se is described in detail below with reference to FIGS. 1b and 3.

Referring to FIG. 2, a portion of the fibers 30 upstream from the scarfing roller 38 is shown to illustrate the preferred distribution of the moisture-absorbent particles 39 within a predetermined thickness of the non-woven pad 32. Immediately upstream from the scarfing roller 38, the fibers 30 atop the conveyor 18 are at a maximum thickness 54, measured between the top surface 56 and bottom surface 58 of the fibers 30. At least a portion 60 of the fibers 30 are removed by the scarfing roller 38, extending from the top surface 56 inwardly, forming a non-woven pad 32 having a uniform, preferred thickness 61 downstream from the scarfing roller 38.

Referring now to both FIGS. 1a and 2, the method of distributing moisture-absorbent particles 39 within a desired layer or portion of the non-woven pad 32 is illustrated. Particle distribution within the non-woven pad 32 is controlled by varying the location of the nozzle 52 along the length of the fibers 30 atop the conveyor 18, and by varying the velocity at which the particles 39 are ejected from the nozzle 52.

Initial or gross adjustment of the particle distribution is obtained by positioning the nozzle 52 between the point 34 at which vacuum is first applied to the conveyor 18 and the point 36 near the scarfing roller 38. For example, if moisture-absorbent particles 39 are desired near the bottom portion or layer of the non-woven pad 32, the nozzle 52 is positioned nearer the point 34 where the non-woven pad 32 is just beginning to be formed. The particles 39 are thus distributed along the lower or bottom layer of the pad 32, after which time additional fibers 30 are drawn onto the conveyor 18 until a maximum thickness of fibers 30 is obtained near the scarfing roller 38. If a distribution of moisture-absorbent particles 39 is desired at a top layer of the non-woven pad 32, the nozzle 52 is positioned near the point 36 of maximum thickness of the fibers 30 atop the conveyor 18 as illustrated in phantom in FIG. 1a. In this position of nozzle 52, particles 39 are distributed among fibers 30 located at a top or upper layer of the pad 32 and only a limited amount of fibers 30 are thereafter drawn onto the conveyor 18 before a maximum thickness of fibers 30 is reached at point 36.

The positioning of nozzle 52 provides only a gross or initial adjustment of particle distribution within the pad 32. More precise adjustment or "fine tuning" of the particle distribution is obtained by controlling the velocity at which the particles 39 are discharged from the nozzle 52. For example, with the nozzle 52 positioned near point 34, as described above, the velocity of the particles 39 ejected from the nozzle 52 is controlled to avoid discharging the particles 39 through the fibers 30 onto the perforated conveyor 18 while ensuring that the particles 39 are intermixed throughout a desired portion of the thickness of the fibers 30. With the nozzle 52 positioned nearer the point of maximum thickness of the fibers 30, as described above, the particle velocity is varied to control the depth of penetration of the particles 39 into the fibers 30. Higher particle velocity results in deeper penetration of particles 39 into the fibers 30 and thus a concentration of particles 39 in a relatively thick layer of the pad 32. Lower particle velocity results in shallower penetration of particles 39 into the fibers 30 and thus a concentration of particles 39 in a relatively thin layer of the pad 32.

Referring now to FIG. 2, a presently preferred particle distribution within non-woven pad 32 is illustrated in which particles 39 are ejected with the nozzle 52 positioned as shown in solid lines in FIG. 1a. In this embodiment, the particle velocity is adjusted for the chosen position of nozzle 52 so that a concentration of particles 39 is obtained in a center portion or layer 57 of the non-woven pad 32 having a predetermined thickness equal to about one-third of the finished thickness 61 of the pad 32. As shown in FIG. 2, the particles 39 are ejected from nozzle 52 at a velocity so that they penetrate inwardly into the pad 32. Additional fibers 30 are thereafter drawn atop the center layer 57 until a maximum thickness 54 is obtained near the scarfing roller 38.

By intermixing the particles 39 with the fibers 30 before a maximum fiber thickness has been reached, a top portion or layer 59 of fibers 30 is formed which is substantially free of moisture-absorbent particles 39. Additionally, by controlling the velocity at which the particles 39 are ejected from nozzle 52, the particles 39 do not penetrate entirely through the fibers 30 but stop at a predetermined depth forming a bottom portion or layer 63 of fibers 30 which is also substantially free of moisture-absorbent particles 39. The nozzle 52 position and particle velocity are therefore chosen in the embodiment of FIG. 2 to produce a non-woven pad 32 having a center layer 57 consisting of intermixed moisture-absorbent particles 39 and fibers 30, which is bounded by layers 59, 63 substantially free of moisture-absorbent particles 39. It should be understood from the foregoing discussion, however, that the position and thickness of the layer of pad 32 having a concentration of moisture-absorbent particles 39 can be varied as desired by changing the nozzle position and particle velocity, and the embodiment of pad 32 illustrated in FIG. 2 is one preferred embodiment.

Of course, some particles 39 may be found in both of the boundary layers 59, 63 due to the nature of the spraying operation. Some particles 39 may cling to the fibers 30 within the top layer 59 as they are ejected from nozzle 52. In addition, some particles 39 may pass through the center layer 57 and enter the bottom layer 63. However, as illustrated in FIG. 2, it is contemplated that the position of nozzle 52 and particle velocity can be adjusted so that only a very small amount of particles 39 fall outside of the center layer 57 and thus the boundary top and bottom layers 59, 63 are "substantially" free of particles 39.

Figure 1B:
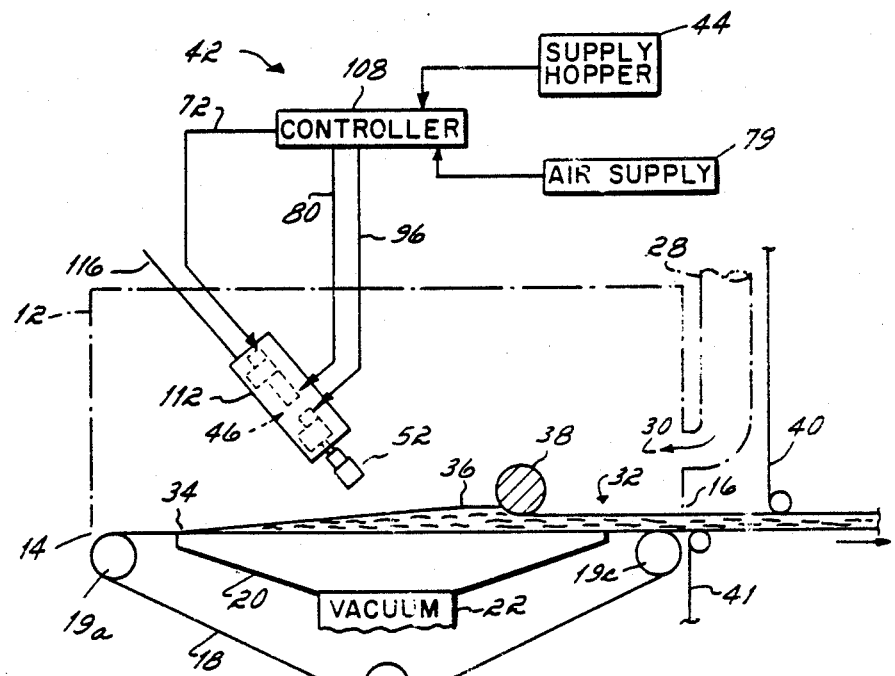
FIG. 1b is a schematic, elevational view of an alternative embodiment of the apparatus of this invention.
Figure 3:
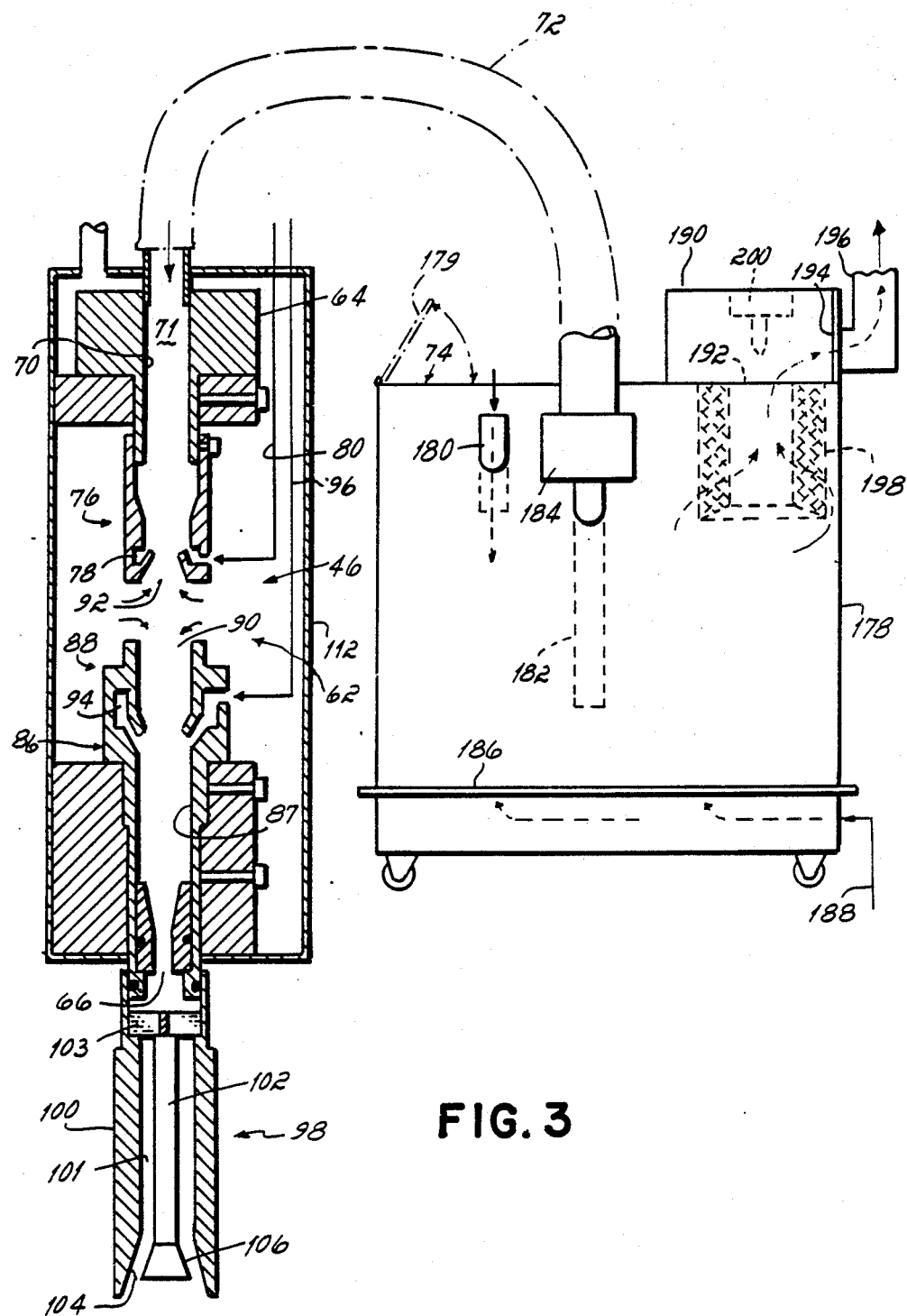
FIG. 3 is a schematic, elevational view in partial cross section of one embodiment of a spray gun system and cartridge feeder of this invention.

Referring now to FIGS. 1b and 3, the illustrated spray gun system 42 is substantially identical to that disclosed in U.S. Pat. No. 4,600,603, owned by the assignee of this invention. The disclosure of that patent is incorporated by reference in its entirety herein. Briefly, the spray gun 46 of spray gun system 42 comprises a barrel 62 having a particle introduction head 64 at one end and a discharge outlet 66 at the opposite end. The particle introduction head 64 is formed with an axial bore 70 having a particle inlet 71 which is connected by a delivery line 72 to a cartridge feeder 74 containing moisture-absorbent particles. The cartridge feeder 74 is discussed in detail below.

An inverted air flow amplifier 76 is mounted to the bottom portion of powder introduction head 64, coaxial with its axial bore 70. The inverted air flow amplifier 76 is formed with an annular channel 78 which is connected to a source 79 of high velocity compressed air by a delivery line 80. See FIG. 1a. The cartridge feeder 74 is operable to pump a stream of air-entrained, moisture-absorbent particles into the particle inlet 71 of the particle introduction head 64 through the axial bore 70 and into the inverted air flow amplifier 76. Low velocity compressed air from line 80 is injected through the annular channel 78 of the inverted air flow amplifier 76 which is operable to impact the air-entrained moisture-absorbent particles with an air flow directed generally upstream within the barrel 62 toward the particle inlet bore 71.

The lower end of barrel 62 as viewed in FIG. 3 is formed with a body portion 86 having an axial bore 87. The upper end of body portion 86 mounts an air flow amplifier 88, and the lower end of body portion 86 forms the discharge outlet 66 of barrel 62 which supports a nozzle 98. The air flow amplifier 88 is formed with an inlet 90 which is spaced from and coaxial with the outlet 92 of the inverted air flow amplifier 76. In addition, the air flow amplifier 88 includes an annular channel 94 connected to the source 79 of high velocity compressed air by a delivery line 96.

In a preferred embodiment, the nozzle 98 mounted to the discharge outlet 66 of barrel 62 comprises an annular sleeve 100 formed with a throughbore 101 within which an internal deflector 102 is concentrically mounted by a support 103. As shown at the bottom of FIG. 3, the discharge end of the annular sleeve 100 is formed with a tapered, conical-shaped wall 104 which parallels a similarly shaped conical wall 106 formed at the end of deflector 102. Moisture-absorbent particles ejected from the discharge outlet 66 of powder spray barrel 62, in a manner described below, enter the throughbore 101 of nozzle 98 and contact the conical-shaped end wall 106 of the internal deflector 102. The end wall 106 of deflector 102 deflects the particles radially outwardly into engagement with the conical wall 104 of the annular sleeve 100.

The nozzle 98 therefor discharges a generally annular pattern of moisture-absorbent particles for intermixing with the fibers 30 forming the non-woven pad 32 having a distribution which is limited in diameter by virtue of the contact of the deflected particles with the conical wall 104 of the annular sleeve 100. By the time the particles 39 reach the non-woven pad 32, the pattern 107 is substantially oval in shape. As shown in FIG. 1d, control of the shape of pattern 107 in a non-woven pad 32 for a disposable diaper, for example, enables the leg holes 109 to be cut and individual diaper pads separated along cut lines 111 without wasting moisture-absorbent particles 39 or dulling cutting dies.

Referring now to FIG. 1b in conjunction with FIG. 3, the operation of spray gun system 42 in practicing the method of this invention is illustrated. A controller 108, operatively connected to the spray gun 46, compressed air source 79 and cartridge feeder 74, directs moisture-absorbent particles from the cartridge feeder 74 into the particle inlet 71 in the spray gun 46. The delivery lines 80, 96 supply high velocity, compressed air from the source 79 to the inverted air flow amplifier 76 and air flow amplifier 88. As described in detail in U.S. Pat. No. 4,600,603, the inverted air flow amplifier 76 evenly distributes the moisture-absorbent particles within the particle spray barrel 62 and in the course of its operation draws at least some ambient air through outlet 92. The air flow amplifier 88 receives the evenly distributed moisture-absorbent particles from the outlet 92 of inverted air flow amplifier 76 and accelerates such particles to the discharge outlet 66 of the gun barrel 62. In the course of its operation, the air flow amplifier 88 also draws at least some ambient air through its inlet 90 to provide sufficient quantities of air to accelerate the moisture-absorbent particles.

In one preferred embodiment, the controller 108 is programmed to operate the spray gun 46 intermittently so that the moisture-absorbent particles are distributed within selected, spaced patterns 107 along the length of non-woven pad 32. See FIG. 1d. Intermittent operation of spray gun 46 is achieved by alternately terminating the supply of moisture-absorbent particles from the feeder 74 to the spray gun 46 and then restarting the flow thereof. The inverted air flow amplifier 76 is constantly supplied with high velocity compressed air from the line 80 so that in periods where the flow of moisture-absorbent particles is terminated, the upstream flow of compressed air provided by the inverted air flow amplifier 76 maintains the moisture-absorbent particles within the particle introduction head 64 and delivery line 72. This prevents drift of the particles toward the discharge end of the barrel and thus produces sharply defined patterns 107 along the non-woven pad 32 impregnated with moisture-absorbent particles and areas having no moisture-absorbent particles.

In some applications, the spray gun 46 is preferably positioned in the interior of the forming chamber 12. In one presently preferred embodiment, illustrated in FIG. 1b, the spray gun 46 is encased within a housing or cannister 112. The cannister 112 is formed with bores to receive the pressurized air delivery lines 80, 96, the inlet conduit 72 from the cartridge feeder 74 and a vent line 116. The vent line 116 extends from the cannister 112 to the exterior of forming chamber 12 to supply ambient air to the air flow amplifiers 76, 88.

As discussed above, both air flow amplifiers 76, 88 draw ambient air therein into the barrel 62 in the course of their operation. The cannister 112 is required to prevent the fibrous particles 30 introduced into the interior of forming chamber 12 from being drawn by the air flow amplifiers 76, 88 into the gun barrel 62. If allowed to enter the barrel 62, the fibrous particles could disrupt the flow of absorbent material particles through the spray gun 46 and produce an unacceptable pattern upon the non-woven pad 32, especially where internal deflectors are employed, such as deflector 106 of FIG. 3.

Figure 1C:
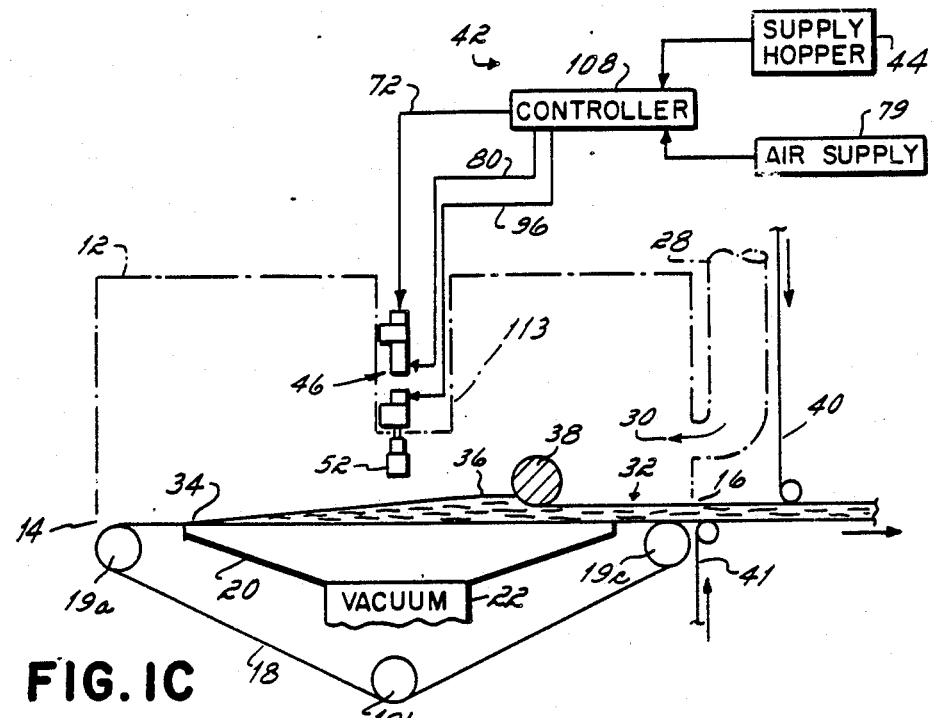
FIG. 1c is a schematic, elevational view of an alternative embodiment to that shown in FIG. 1b.
Figure 1D:
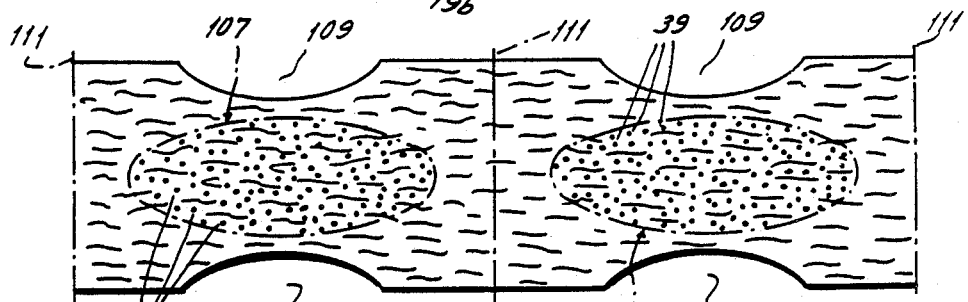
FIG. 1d is a plan view of the non-woven pad of fibrous particles intended for use as a disposable diaper, having moisture-absorbent material at selected areas therealong.

In an alternative embodiment illustrated in FIG. 1c, a duct 113 extends into the forming chamber 12 which is open at the op of the chamber 12. The duct 113 mounts the spray gun 46 in position above the fibers 30 atop the conveyor 18 and isolates it from the fiber-laden air within the forming chamber 12 while permitting access to the spray gun 46 for maintenance.

Figure 4:
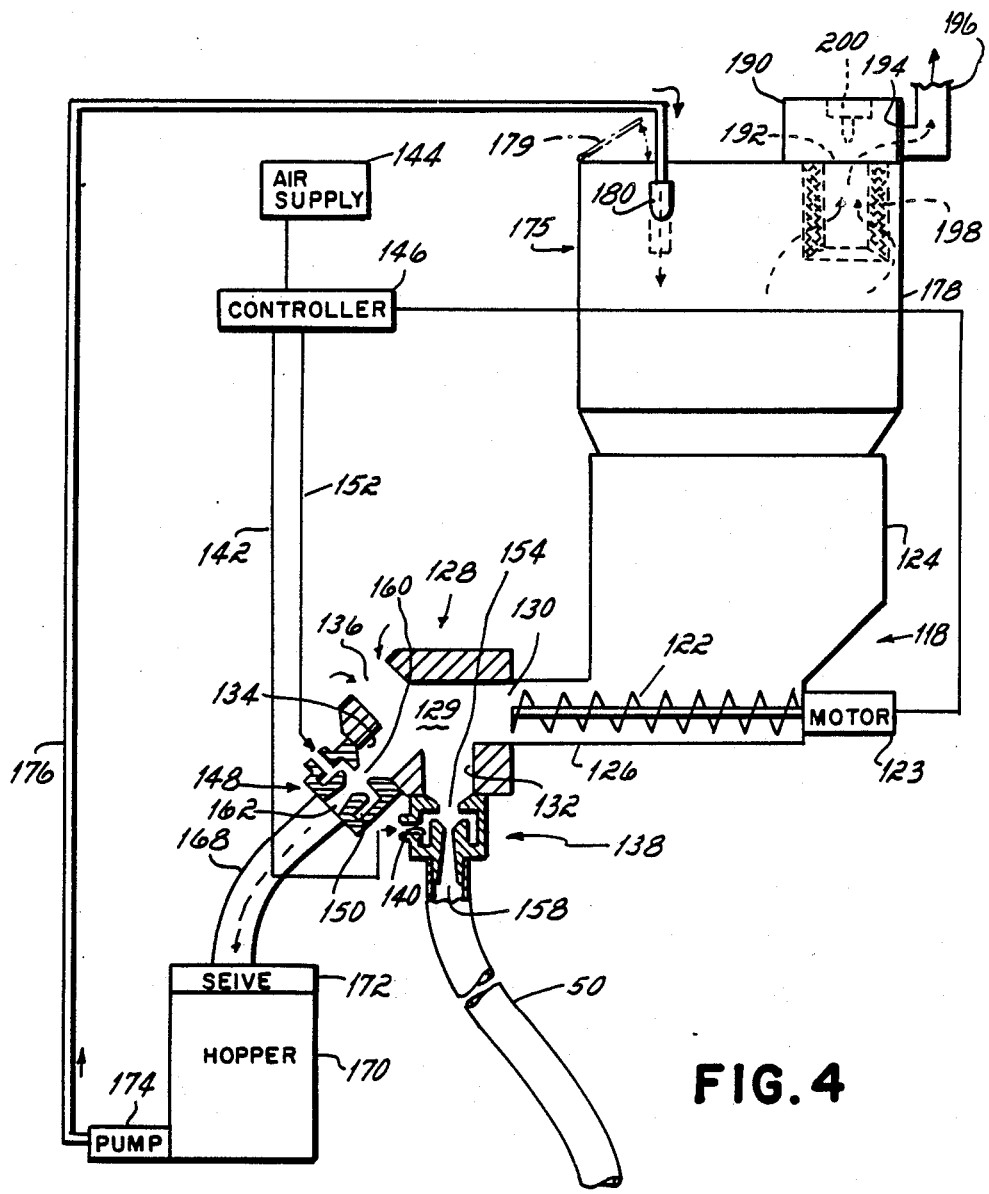
FIG. 4 is a schematic, elevational view in partial cross section of an alternative embodiment of a spray gun system and cartridge feeder in accordance with this invention.

Referring now to FIG. 4, an alternative embodiment of a spray gun system for practicing the method of this invention is illustrated. The spray gun system 118 of this embodiment is substantially identical to that disclosed in U.S. Pat. No. 4,770,344, issued Sep. 13, 1988, entitled "Powder Spraying System", which is owned by the same assignee as this invention. The disclosure of U.S. Pat. No. 4,770,344 is incorporated by reference in its entirety herein.

Briefly, the spray gun system 118 comprises a dry material feeding device having an auger or screw 122 mounted at the base of a feed hopper 124 which is rotated by a motor 123. The rotating screw 122 is operable to remove an accurately metered quantity of moisture-absorbent particles from the feed hopper 124 and discharge them through an outlet 126.

The moisture-absorbent particles are transmitted to a manifold block 128 formed with an internal cavity 129, an inlet passageway 130 connected to the outlet 126 of feed hopper 124, an outlet passageway 132, a return passageway 134 and a vent passageway 136. Each of the passageways 130, 132, 134 and 136 are connected to the internal cavity 129 of manifold 128. A first air flow amplifier 138 is mounted to the manifold 128 at the outlet passageway 132. The first air flow amplifier 138 is formed with an annular channel 140 connected by a line 142 to a source 144 of high velocity compressed air 144 via a controller 146. An identical, second air flow amplifier 148 is mounted to the manifold 128 at the return passageway 134 whose annular channel 150 is connected to the controller 146 through a line 152.

In one preferred embodiment, the first air flow amplifier 138 has an inlet 154 communicating with the internal cavity 129 and an outlet 158 connected to a flexible tube 50 which extends into the interior of the forming chamber 12. The second air flow amplifier 148 has an inlet 160 which also communicates with the internal cavity 129, and an outlet 162 connected through a line 168 to a dump hopper 170 through a sieve 172. A pump 174 is connected to the dump hopper 170 and communicates with an alternative embodiment of the cartridge feeder 175, described in detail below, through a connector line 176.

The operation of spray gun system 118 in practicing the method of this invention is as follows. Moisture-absorbent particles are continuously introduced into the internal cavity 129 of the manifold 128 through the inlet passageway 130 therein which is connected to the outlet 126 of feed hopper 124. The controller 146 operates to supply high velocity compressed air to the first air flow amplifier 138 through line 142 to create a suction within the internal cavity 129. Ambient air is drawn through the vent passageway 136 into the internal cavity 129 which forms an air-entrained stream of moisture-absorbent particles therein. This air-entrained stream of moisture-absorbent particles is then drawn into the outlet passageway 132 and through the inlet 154 of first air flow amplifier 138. In the course of passage through the first air flow amplifier 138, the air-entrained stream of moisture-absorbent particles is impacted by a stream of high velocity compressed air from line 142 and is accelerated through the flexible tube 50 for intermixing with the fibers 30 forming the non-woven pad 32.

In order to intermittently discharge moisture-absorbent particles, the controller 146 is operable to alternately close the flow of high velocity air to the first air flow amplifier 138 and open the flow of high velocity air to the second air flow amplifier 148. The second air flow amplifier 148 operates identically to the first air flow amplifier 138 described above. When operated, it suctions moisture-absorbent particles from the internal cavity 129 of manifold 128 through the line 168 to the dump hopper 170. The moisture-absorbent particles are then recirculated from the dump hopper 170 by pump 174 into the cartridge feeder 175. Alternatively, the line 168 is directly connected to a sieve (not shown) mounted within the cartridge feeder 175 at the inlet 180. This prevents drifting of particles from the internal cavity 129 through the outlet passageway 132 when the first air flow amplifier 138 is not operated. Flow of moisture-absorbent particles into the chamber 12 is restored by simultaneously terminating the flow of high velocity compressed air to the second air flow amplifier 148 and starting the flow of high velocity compressed air to the first air flow amplifier 138.

The alternating operation of the first and second air flow amplifiers 138, 148 provides for the sharp termination of the flow of moisture-absorbent particles into the chamber 12 and the subsequent sharply defined restarting of such flow as desired. This produces discrete patterns 107 along the non-woven pad 32 which are interspersed with moisture-absorbent particles 39, and other areas having no moisture-absorbent particles 39 at all.

Referring now to FIG. 3, one embodiment of a cartridge feeder 74 is illustrated in combination with the spray gun system 42. A detailed description of the cartridge feeder 74 per se is provided in U.S. Pat. No. 4,730,647 issued Mar. 15, 1988, and entitled "Powder Feeder Apparatus", which is incorporated by reference in its entirety herein.

The cartridge feeder 74 illustrated in FIG. 3 comprises a housing 178, an inlet 180 connected to a source (not shown) of moisture-absorbent particles and an outlet 182 connected to a pump 184. The top wall of the housing 178 is formed with a hinged door 179 which provides an outlet for the otherwise closed housing 178 in the event of an explosion therein. A fluidizing bed 186 is mounted at the base of housing 178 which is supplied with fluidizing air through a feed line 188. Referring to the top righthand portion of the cartridge feeder 74 in FIG. 3, a clean air chamber 190 is mounted atop the housing 178 which is formed with an inlet 192 communicating with the interior of housing 178 and an exterior outlet 194 connected to a vacuum line 196. A cartridge filter 198 is mounted within the housing 178 over the inlet 192 to the clean air chamber 190. A jet cleaning valve 200 is positioned in the clean air chamber 190 directly above the cartridge filter 198.

The unitized feeder 74 is operable to supply a stream of air-entrained, moisture-absorbent particles through the feed conduit 72 to the inlet 71 in the spray gun 46. Moisture-absorbent particles are first introduced into the interior of housing 178 via the inlet 180. The particles descend into the fluidizing bed 186 where they are fluidized by a low pressure air stream from the feed line 188 which moves upwardly through the fluidizing bed 186 in a well known manner. The pump 184 removes the fluidized moisture-absorbent particles from the housing 178 and forms an air-entrained stream of moisture-absorbent particles which is transmitted through feed conduit 72 to the spray gun 46.

In order to prevent a pressure buildup within the housing 178 from the supply of fluidizing air to the fluidizing bed 186, the housing 178 must be properly vented. This is achieved by operation of the clean air chamber 190. In the preferred embodiment, the vacuum line 196 from the clean air chamber 190 is connected to the vacuum source 22 at the base of forming chamber 12. The vacuum source 22 operates to draw air from the interior of housing 178 to vent the housing 178. Any moisture-absorbent particles floating within the interior of housing 178 are filtered by the cartridge filter 198 so that only clean, filtered air enters the clean air chamber 190 from the interior of housing 178. The cartridge filter 198 is periodically cleaned of collected moisture-absorbent particles by the jet cleaning valve 200 which ejects a pressurized jet of gas in the reverse direction onto cartridge filter 198 to blow the collected particles back into the housing 178.

Referring now to FIG. 4, an alternative embodiment of a cartridge feeder 175 is illustrated. This embodiment is also disclosed in detail in U.S. Pat. No. 4,730,647 issued Mar. 15, 1988, and entitled "Powder Feeder Apparatus", as mentioned above. In this embodiment, the cartridge feeder 175 is similar to that disclosed in FIG. 3 except the fluidizing plate 186 and pump 184 are eliminated. In addition, one other modification which can be made in this embodiment is that if the system operation results in the development of a positive pressure within the hopper 170, both the hopper 170 and sieve 172 could be located within the cartridge feeder 175 which is under negative pressure. This prevents moisture-absorbent particles from being directed back into the manifold 129 through line 168. Other than these differences, the embodiment illustrated in FIG. 4 is the same as shown in FIG. 3, and the same reference numbers are therefor repeated in the embodiment of FIG. 4 for those elements common to the FIG. 3 embodiment.

Moisture-absorbent particles are introduced into the cartridge feeder 175 of FIG. 4 through a connector line 176 connected to the dump hopper 170 of the spray gun system 118. The base of housing 178 is mounted atop the feed hopper 124. The moisture-absorbent particles therefore pass completely through the housing 178 into the feed hopper 124 for delivery by the rotating screw 122 into the manifold 128. The remaining elements of the cartridge feeder 175 described above, including the manner in which housing 178 is vented, are identical in structure and function to the embodiment shown in FIG. 3.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

We claim:

1. Apparatus for forming a non-woven pad of fibrous material with particulate material interspersed throughout a selected portion of the thickness of said non-woven pad, comprising:

a chamber having an inlet and an outlet;

a conveyor movable between said inlet and said outlet of said chamber;

means for introducing fibrous material into said chamber;

vacuum means located beneath said conveyor for applying a vacuum in said chamber to draw said fibrous material onto said conveyor, said fibrous material forming a non-woven pad on said conveyor which increases in thickness in a direction from said inlet of said chamber toward said outlet thereof, said non-woven pad having a bottom surface resting atop said conveyor and a top surface which slopes upwardly relative to said conveyor from said inlet of said chamber toward said outlet thereof;

dispenser means disposed within said chamber above said conveyor at a predetermined location along said upwardly sloping top surface of said non-woven pad for intermixing particulate material with a portion of said fibrous material being drawn onto said conveyor at said predetermined location to form a layer of intermixed fibrous material and particulate material within a predetermined portion of said thickness of said non-woven pad while maintaining another portion of said thickness of said non-woven pad substantially free of said particulate material.

2. Apparatus for forming a non-woven pad of fibrous material with particulate material interspersed throughout a selected portion of the thickness of said non-woven pad at spaced locations therealong, comprising:

a chamber having an inlet and an outlet;

a conveyor movable between said inlet and said outlet of said chamber;

means for introducing fibrous material into said chamber;

vacuum means located beneath said conveyor for applying a vacuum in said chamber to draw said fibrous material onto said conveyor, said fibrous material forming a non-woven pad on said conveyor which increases in thickness in a direction from said inlet of said chamber toward said outlet thereof;

dispenser means disposed at a predetermined location above said conveyor and within said chamber between said inlet and outlet thereof for intermittently mixing said particulate material with a portion of said fibrous material being drawn onto said conveyor to form a layer of intermixed fibrous material and particulate material within a predetermined portion of the thickness of said non-woven pad at spaced locations therealong while maintaining another portion of the thickness of said pad at said spaced locations therealong substantially free of said particulate material.

3. Apparatus for forming a non-woven pad of fibrous material with particulate material interspersed throughout a selected portion of the thickness of said non-woven pad, comprising:

a chamber having an inlet and an outlet;

a conveyor movable between said inlet and said outlet of said chamber;

means for introducing fibrous material into said chamber;

vacuum means located beneath said conveyor for applying a vacuum in said chamber to draw said fibrous material onto said conveyor, said fibrous material forming a non-woven pad on said conveyor which increases in thickness in a direction from said inlet of said chamber toward said outlet thereof;

a spray gun for intermixing said particulate material with a portion of said fibrous material being drawn onto said conveyor, said spray gun comprising:

a gun barrel having an inlet end and a discharge end disposed at a predetermined location above said conveyor and within said chamber between said inlet and outlet thereof;

means for connecting said inlet end to a source of air-entrained, particulate material;

first air flow amplifier means carried by said gun barrel for impacting said air-entrained, particulate material with a high velocity stream of compressed air directed generally upstream of said gun barrel; and second air flow amplifier means carried by said gun barrel downstream of said first air flow amplifier means, said second air flow amplifier means being operable to impact said air-entrained particulate material with a stream of compressed air for accelerating said air-entrained, particulate material, said air-entrained, particulate material being ejected from said discharge end of said gun barrel and intermixing with said fibrous material to form a layer of intermixed fibrous material and particulate material within a predetermined portion of the thickness of said non-woven pad while maintaining another portion of the thickness of said non-woven pad substantially free of said particulate material.

4. The apparatus of claim 3 in which said spray gun comprises:

a nozzle mounted to said discharge end of said gun barrel; and a substantially closed housing encasing said spray gun, said housing including a vent line connected thereto having an outer end extending outside of said chamber for providing ambient air to said first and second air flow amplifier means.

5. The apparatus of claim 4 in which said nozzle comprises:

an annular barrel having a throughbore, said annular barrel being formed with an inlet end and a radially outwardly tapered outlet end;

a deflector formed with a radially outwardly tapered end;

means for mounting said deflector within said throughbore of said barrel so that said tapered end of said deflector is concentric with said tapered outlet end of said annular barrel.

6. The apparatus of claim 3 further including a duct extending into said chamber, said spray gun being mounted within said duct to isolate said spray gun from said fibrous material within said chamber.

7. The apparatus of claim 3 in which said spray gun is mounted outside of said chamber, said spray gun further including an elongated, bendable conduit connected at a first end to said discharge end of said gun barrel, a second end of said bendable conduit extending into said chamber for intermixing said particulate material with said fibrous material forming said non-woven pad.

8. The apparatus of claim 3 in which said means for connecting said inlet end of said spray gun to a source of particulate material includes control means for terminating and restarting the flow of said particulate material to said inlet end of said spray gun while maintaining the flow of compressed air to said first air amplifier means, whereby the flow of particulate material from said discharge end of spray gun into said non-woven pad is sharply terminated and restarted for intermixing the particulate material with a portion of said fibrous material being drawn onto said conveyor to form a layer of intermixed fibrous material and particulate material within predetermined portion of the thickness of said non-woven pad at spaced locations therealong.

9. The apparatus of claim 3 in which said source of air-entrained particulate material comprises:

a housing having an interior formed with an inlet and an outlet;

a fluidized bed mounted in said interior of said housing for receiving particulate material transmitted into said interior of said housing through said inlet, said fluidized bed being operable to fluidize said particulate material; and vent means communicating with said interior of said housing, said vent means being connected to said vacuum means for venting said interior of said housing.

10. The apparatus of claim 9 in which said vent means comprises:

a clean air chamber mounted to said housing, said clean air chamber being formed with an inlet communicating with said interior of said housing and an outlet connected to said vacuum means, said vacuum means being operable to create a negative pressure within said clean air chamber to draw air from said interior of said housing into said clean air chamber to vent said housing;

a cartridge filter mounted within said housing and connected to said inlet of said clean air chamber, said cartridge filter removing any particulate material entrained in the air drawn by said vacuum means from said closed interior of said housing.

11. Apparatus for forming a non-woven pad of fibrous material with particulate material interspersed throughout a selected portion of the thickness of said non-woven pad, comprising:

a chamber having an inlet and an outlet;

a conveyor movable between said inlet and said outlet of said chamber;

means for introducing fibrous material particles into said chamber;

vacuum means located beneath said conveyor for applying a vacuum in said chamber to draw said fibrous material onto said conveyor, said fibrous material forming a non-woven pad on said conveyor which increases in thickness in a direction from said inlet of said chamber toward said outlet thereof;

dispenser means for intermixing said particulate material with a portion of said fibrous material being drawn onto said conveyor, said dispenser means comprising:

a manifold having an internal cavity, said manifold being formed with a vent passageway open to atmosphere, an inlet passageway, an outlet passageway, and a return passageway, each of said passageways being connected to said internal cavity;

supply means connected to a source of said particulate material, said supply means communicating with said inlet passageway for transporting a metered quantity of said particulate material into said internal cavity of said manifold;

first air amplifier means connected to said outlet passageway for drawing ambient air through said vent passageway of said manifold into said internal cavity to form a stream of air-entrained, particulate material within said internal cavity;

a conduit connected at one end to said first air amplifier means and having an opposite end disposed at a predetermined location above said conveyor and within said chamber between said inlet and outlet thereof, said first air amplifier means drawing said stream of air-entrained, particulate material from said internal cavity through said outlet passageway and into said conduit, said first air amplifier means impacting said stream of air-entrained, particulate material with a high velocity air stream to accelerate said stream of air-entrained, particulate material through said conduit for intermixing with said fibrous material to form a layer of intermixed fibers and particulate material within a predetermined portion of the thickness of said non-woven pad while maintaining another portion of the thickness of said non-woven pad substantially free of said particulate material;

second air amplifier means connected to said return passageway of said manifold for drawing ambient air through said vent passageway into said internal cavity to form a stream of air-entrained, particulate material within said internal cavity, said second air amplifier means drawing said stream of air-entrained, particular material from said internal cavity through said return passageway and into a return line communicating with said supply means;

control means communicating with each of said first and second air amplifiers for simultaneously operating one of said first and second air amplifiers and closing the other so that said stream of air-entrained, particulate material flows from said internal cavity of said manifold into either said conduit or said return line.

12. The apparatus of claim 11 in which said source of particulate material comprises:

a housing having a top wall, sidewalls and an open bottom defining a hollow interior, said housing being mounted to said supply means so that said hollow interior of said housing communicates with said supply means through said open bottom of said housing;

means for introducing said particulate material into said housing;

vent means communicating with said interior of said housing, said vent means being connected to said vacuum means for venting said hollow interior of said housing.

13. Apparatus for forming a non-woven pad of fibrous material with a particulate material interspersed throughout a selected portion of the thickness of said non-woven pad, comprising:

a chamber having an inlet and an outlet;

a conveyor movable between said inlet and said outlet of said chamber;

means for introducing fibrous material into said chamber;

vacuum means located beneath said conveyor for applying a vacuum in said chamber to draw said fibrous material onto said conveyor, said fibrous material forming a non-woven pad on said conveyor which increases in thickness in a direction from said inlet of said chamber toward said outlet thereof, said non-woven pad having a bottom surface resting atop said conveyor and a top surface which slopes upwardly relative to said conveyor from said inlet of said chamber toward said outlet thereof;

a source of supply for said particulate material;

transport means for transporting said particulate material from said source of supply;

dispenser means connected to said transport means to receive said particulate material, said dispenser means being disposed within said chamber above said conveyor at a predetermined location along said upwardly sloping top surface of said non-woven pad for intermixing said particulate material with a portion of said fibrous material being drawn onto said conveyor at said predetermined location to form a layer of intermixed fibrous material and said particulate material within a predetermined portion of said thickness of said non-woven pad while maintaining another portion of said thickness of said non-woven pad substantially free of said particulate material;

control means for controlling the operation of said dispenser means.

14. The apparatus of claim 13 in which said source of supply for said particulate material comprises:

a housing having an interior formed with an inlet and an outlet;

a fluidized bed mounted in said interior of said housing for receiving said particulate material transmitted into said interior of said housing through said inlet, said fluidized bed being operable to fluidize said particulate material; and vent means communicating with said interior of said housing, said vent means being connected to said vacuum means for venting said interior of said housing.

15. The apparatus of claim 13 in which said means for transporting said particulate material from said source of supply comprises a screw feeder mounted at the base of said source of supply and connected to said dispenser means.

16. The apparatus of claim 13 in which said dispenser means is a spray gun comprising:
a gun barrel having an inlet end and a discharge end located within said chamber;
means for connecting said inlet end to said source of supply of said particulate material;
first air flow amplifier means carried by said gun barrel for impacting said particulate material with a high velocity stream of compressed air directed generally upstream of said gun barrel; and
second air flow amplifier means carried by said gun barrel downstream of said first air flow amplifier means, said second air flow amplifier means being operable to impact said particulate material with a stream of compressed air in the course of passage therethrough for accelerating said particulate material, said particulate material being ejected from said discharge end of said gun barrel into said non-woven pad of fibrous material as said non-woven pad is being formed in said chamber.

17. Apparatus for forming a non-woven pad of fibrous material with a particulate material interspersed throughout a selected portion of the thickness of said non-woven pad, comprising:
a chamber having an inlet and an outlet;
a conveyor movable between said inlet and said outlet of said chamber;
means for introducing fibrous material into said chamber;
vacuum means located beneath said conveyor for applying a vacuum in said chamber to draw said fibrous material onto said conveyor, said fibrous material forming a non-woven pad on said conveyor which increases in thickness in a direction from said inlet of said chamber toward said outlet thereof, said non-woven pad having a bottom surface resting atop said conveyor and a top surface which slopes upwardly relative to said conveyor from said inlet of said chamber toward said outlet thereof;
a hopper for supplying said particulate material;
a pump connected to said hopper for pumping said particulate material from said hopper;
a spray gun connected to said pump for receiving said particulate material from said hopper, said spray gun being disposed within said chamber above said conveyor at a predetermined location along said upwardly sloping top surface of said non-woven pad for intermixing said particulate material with a portion of said fibrous material being drawn onto said conveyor at said predetermined location to form a layer of intermixed fibrous material and said particulate material within a predetermined portion of said thickness of said non-woven pad while maintaining another portion of said thickness of said non-woven pad substantially free of said particulate material;
a control for controlling the operation of said spray gun.

18. Apparatus for use with a forming chamber having an inlet and an outlet, a conveyor movable between said inlet and said outlet, a vacuum device located beneath said conveyor for applying a vacuum in said chamber to draw fibrous material introduced into said chamber onto said conveyor forming a non-woven pad on said conveyor which has a bottom surface resting atop said conveyor and a top surface which slopes upwardly relative to said conveyor from said inlet of said chamber to said outlet thereof, said apparatus comprising:
a source of supply for a particulate material;
transport means for transporting said particulate material from said source of supply;
dispenser means connected to said transport means to receive said different particulate material, said dispenser means being adapted to be positioned within said chamber above said conveyor at a predetermined location along said upwardly sloping top surface of said non-woven pad;
control means for causing said dispenser means to intermix said particulate material with a portion of said fibrous material being drawn onto said conveyor at said predetermined location to form a layer of intermixed fibrous material and said particulate material within a predetermined portion of the thickness of said non-woven pad while maintaining another portion of the thickness of said non-woven pad substantially free of said particulate material.

19. The apparatus of claim 18 in which said source of supply for said particulate material comprises:
a housing having an interior formed with an inlet and an outlet;
a fluidized bed mounted in said interior of said housing for receiving said particulate material transmitted into said interior of said housing through said inlet, said fluidized bed being operable to fluidize said particulate material; and
vent means communicating with said interior of said housing, said vent means being connected to said vacuum means for venting said interior of said housing.

20. The apparatus of claim 17 in which said means for transporting said particulate material from said source of supply comprises a screw feeder mounted at the base of said source of supply and connected to said dispenser means.

21. The apparatus of claim 17 in which said dispenser means is a spray gun comprising:
a gun barrel having an inlet end and a discharge end located within said chamber;
means for connecting said inlet end to said source of supply of said particulate material;
first air flow amplifier means carried by said gun barrel for impacting said particulate material with a high velocity stream of compressed air directed generally upstream of said gun barrel; and
second air flow amplifier means carried by said gun barrel downstream of said first air flow amplifier means, said second air flow amplifier means being operable to impact said particulate material with a stream of compressed air in the course of passage therethrough for accelerating said particulate material, said particulate material being ejected from said discharge end of said gun barrel into said nonwoven pad of fibrous material as said non-woven pad is being formed in said chamber.

22. The apparatus of claim 18 in which a stream of pressurized air is supplied to said dispenser means, said control means including means for turning said stream of pressurized air on and off.

23. The apparatus of claim 18 in which a stream of pressurized air is supplied to said dispenser means, said control means including at least one pressure regulator for controlling the pressure of said stream of pressurized air.

24. Apparatus for use with a forming chamber having an inlet and an outlet, a conveyor movable between said inlet and said outlet, a vacuum device located beneath said conveyor for applying a vacuum in said chamber to draw fibrous material introduced into said chamber onto said conveyor forming a non-woven pad on said conveyor which has a bottom surface resting atop said conveyor and a top surface which slopes upwardly relative to said conveyor from said inlet of said chamber to said outlet thereof, said apparatus comprising:
- a hopper for supplying a particulate material;
- a pump connected to said hopper for pumping said particulate material from said hopper;
- a spray gun connected to said pump for receiving said particulate material from said hopper, said spray gun being adapted to be positioned within said chamber above said conveyor at a predetermined location along said upwardly sloping top surface of said non-woven pad;
- a control for causing said spray gun to intermix said particulate material with a portion of said fibrous material being drawn onto said conveyor at said predetermined location to form a layer of intermixed fibrous material and said particulate material within a predetermined portion of the thickness of said non-woven pad while maintaining another portion of the thickness of said non-woven pad substantially free of said particulate material.

25. Apparatus for forming a non-woven pad of a first material with a second material interspersed throughout a selected portion of the thickness of said non-woven pad, comprising:
- a chamber having an inlet and an outlet;
- a conveyor movable between said inlet and said outlet of said chamber;
- means for introducing said first material in suspension into said chamber;
- vacuum means located beneath said conveyor for applying a vacuum in said chamber to draw said first material onto said conveyor, said first material forming a non-woven pad on said conveyor which has a minimum thickness at said inlet of said chamber and which increases in thickness toward said outlet thereof as more of said first material is drawn onto said conveyor;
- dispenser means disposed within said chamber above said conveyor at a predetermined location along said non-woven pad intermediate said inlet and outlet for intermixing said second material with a portion of said first material being drawn onto said conveyor at said predetermined location, whereby said non-woven pad is formed with a bottom layer of said first material which is drawn onto said conveyor between said inlet of said chamber and said dispenser means, an intermediate layer of intermixed first material and second material which is drawn atop said bottom layer of first material at said predetermined location of said dispenser means, and a top layer of first material which is drawn onto said intermediate layer between said dispenser means and said outlet of said chamber, said bottom layer and said top layer of said non-woven pad being substantially free of said second material.

26. The apparatus of claim 25 in which said dispenser means is operative intermittently to intermix said second material with a portion of said first material being drawn onto said conveyor to form said intermediate layer of intermixed first material and second material within a predetermined portion of the thickness of said non-woven pad at spaced locations therealong.

* * * * *